United States Patent [19]

Mikami et al.

[11] Patent Number: 5,892,102

[45] Date of Patent: Apr. 6, 1999

[54] CATALYST USED IN PRODUCTION OF CARBOXYLIC ACID ESTERS AND PROCESS FOR PRODUCING THESE ESTERS

[75] Inventors: Yuji Mikami; Akio Takeda; Motomu Oh-Kita, all of Otake, Japan

[73] Assignee: Mitsubishi Rayon Co., Ltd., Tokyo, Japan

[21] Appl. No.: 903,417

[22] Filed: Jul. 30, 1997

[51] Int. Cl.$^6$ ............................. B01J 31/04; B01J 23/62; C07C 67/00
[52] U.S. Cl. ............................ 560/210; 502/170; 502/226; 502/329; 560/238; 560/208
[58] Field of Search ............................ 560/210, 208, 560/238; 502/170, 226, 329

[56] References Cited

U.S. PATENT DOCUMENTS 4,356,316  10/1982  Aoshima et al. ................. 560/208
4,520,125   5/1985  Baer et al. .

FOREIGN PATENT DOCUMENTS 0 199 530  10/1986  European Pat. Off. .
57-50545    3/1982  Japan .
57-19090    4/1982  Japan .
57-35856    7/1982  Japan .
57-35860    7/1982  Japan .
61-243044  10/1986  Japan .
61-60820   12/1986  Japan .
62-7902     2/1987  Japan .
4-72578    11/1992  Japan .
5-148184    6/1993  Japan .
9-38506     2/1997  Japan .

*Primary Examiner*—Paul J. Killos
*Attorney, Agent, or Firm*—Oblon, Spivak, McClelland, Maier & Neustadt, P.C.

[57] ABSTRACT

A catalyst for the production of carboxylic acid esters for use in reacting an aldehyde with an alcohol in a liquid phase in the presence of molecular oxygen, comprising calcium carbonate and palladium, bismuth and at least one element selected from the group consisting of barium, iron, zinc and germanium, these elements being supported on said calcium carbonate.

6 Claims, No Drawings

CATALYST USED IN PRODUCTION OF CARBOXYLIC ACID ESTERS AND PROCESS FOR PRODUCING THESE ESTERS

BACKGROUND OF THE INVENTION

1. Field of the Invention

The present invention relates to a process for producing carboxylic acid esters from aldehydes and alcohols by one-step reaction, and a catalyst used in such process. More particularly, the invention pertains to a process for producing methacrylic esters or acrylic esters of high industrial value from methacrolein or acrolein in an economically advantageous way, and a catalyst used in this process.

2. Description of the Related Art

For the production of carboxylic acid esters such as methacrylic esters and acrylic esters, there has been available an industrially established process in which methacrolein or acrolein, which is an aldehyde, is subjected to gas phase catalytic oxidation to produce a methacrylic or acrylic acid which is a carboxylic acid, and it is further subjected to an esterification reaction with an alcohol to produce a methacrylic or acrylic ester.

This process, however, has disadvantages in that it necessitates large production equipment as this process involves two-step (oxidation and esterification) reaction operations. Another problem of this process is poor performance of the catalyst used in the reactions. In production of a methacrylic ester according to this process, a heteropoly-acid salt type catalyst composed mainly of phosphorus and molybdenum is used in the step of oxidizing methacrolein to produce methacrylic acid, but this catalyst is unsatisfactory in durability and yield of product.

Studies are underway on the methods for producing carboxylic acid esters in a high yield by one-step liquid phase reaction from an aldehyde and an alcohol. Various catalysts have been proposed for use in these methods. For example, JP-B-57-35856 proposes Pd- and Pb-based catalysts using calcium carbonate as carrier, JP-B-4-72578 proposes Pb-based catalysts using zinc oxide as carrier, JP-A-57-50545 and JP-A-61-243044 propose various types of Pd- and Pb-based catalysts, JP-B-61-60820 proposes Pd- and Bi-based catalysts, JP-B-62-7902 and JP-A-5-148184 propose the catalysts composed Pd and at least one element selected from Pb and Bi, etc., JP-B-57-35860 proposes Pd-, Tl- and Hg-based catalysts, and JP-B-57-19090 proposes Pd-, alkaline earth metal-, Zn- and Cd-based catalysts.

The Pd-based catalysts decreasse in activity in long-time use since Pd in the catalyst is oxidized in the reaction, so that these catalysts need to be regenerated for continuous use. As means for activating the catalysts, there is proposed, in JP-A-9-38506 for instance, use of formalin, formic acid, hydrazine, methanol and molecular hydrogen in the presence of a Pb-containing substance in preparation of Pd- and Pb-based catalysts. This method, however, is only applicable to preparation of a new catalyst; there is known no established method for regenerating for reusing a catalyst which has decreased in activity in use for reactions.

The carboxylic acid ester production processes using a catalyst such as mentioned above also have the following problems: the reaction rate is low; the objective carboxylic acid ester is obtained as a low-concentration alcohol solution; many by-products such as methyl formate are formed; catalyst life is short; yield of the product is unsatisfactory. Thus, further improvements of these processes have been desired.

SUMMARY OF THE INVENTION

The present invention is envisioned to provide the catalysts that can be used advantageously for preparation of carboxylic acid esters by one-step liquid phase reaction of aldehydes and alcohols in the presence of molecular oxygen, and a process for preparing carboxylic acid esters by using said catalysts.

The catalysts provided according to the present invention are specifically those defined in (1)–(4) below which are used in the reaction of aldehydes and alcohols in a liquid phase in the presence of molecular oxygen:

(1) A catalyst for use in production of carboxylic acid esters, comprising calcium carbonate as carrier and palladium, bismuth and at least one element selected from the group consisting of barium, iron, zinc and germanium, these elements being supported on the calcium carbonate;

(2) A catalyst for use in production of carboxylic acid esters, comprising calcium carbonate as carrier and palladium, bismuth, lead and at least one element selected from the group consisting of barium, iron, zinc and germanium, these elements being supported on the calcium carbonate;

(3) A catalyst for use in production of carboxylic acid esters, comprising calcium carbonate as carrier and palladium, lead and at least one element selected from the group consisting of chromium, iron, cobalt, zinc and silver, these elements being supported on the calcium carbonate;

(4) A catalyst for use in production of carboxylic acid esters, comprising zinc oxide as carrier and palladium, bismuth and at least one element selected from the group consisting of lead, iron, manganese, cobalt, nickel, copper, zinc, germanium, barium and tellurium, these elements being supported on the zinc oxide.

The present invention also provides a process for producing carboxylic acid esters comprising use of at least one type of catalyst selected from those defined in (1)–(4) above.

The present invention further provides a process for producing carboxylic acid esters comprising use of a catalyst which has decreased in activity after use in said production process but has been regenerated by treating it at 0°–100° C. for 0.1–50 hours in the presence of a reducing agent.

PREFERRED EMBODIMENTS OF THE INVENTION

The catalysts used in production of carboxylic acid esters according to the present invention comprise metals and/or metal compounds supported on a carrier comprising calcium carbonte or zinc oxide. In these catalysts, calcium carbonate is used as carrier, but calcium carbonate itself also serves as a catalyst component. The catalysts used in production of carboxylic acid esters according to the present invention are described in detail below.

As the component materials of the metals and/or metal compounds used for the preparation of the catalysts of the present invention, there can be used palladium acetate, palladium chloride, palladium nitrate, palladium sulfate, palladium ammonium chloride, palladium-ammine complex salts and the like as palladium component; bismuth acetate, bismuth carbonate, bismuth chloride, bismuth nitrate, bismuth sulfate and the like as bismuth component; lead acetate, lead carbonate, lead chloride, lead nitrate, lead sulfate, lead tartrate, lead citrate and the like as lead component; and ordinary metal compounds such as acetates, carbonates, nitrates, sulfates, oxalates, chlorides, hydroxides, etc., of the corresponding metals as metal component.

The amount of the metal and/or metal compound to be supported on the carrier, calculated as metal element, is 1–15 parts by weight, preferably 3–13 parts by weight for palladium, 0.1–15 parts by weight, preferably 0.5–12 parts by weight for bismuth and lead, and 0.1–7 parts by weight, preferably 0.3–5 parts by weight for other metals, per 100 parts by weight of the carrier.

The catalysts of the present invention can be prepared by the conventional methods. A process for preparing a catalyst having palladium, bismuth and iron supported on calcium carbonate is explained below as an example. First, calcium carbonate powder is put into water, followed by addition of a predetermined amount of a palladium chloride solution, and the mixture is stirred. The produced suspension is reduced with a reducing agent such as formalin, causing precipitation of metallic palladium. The precipitate is filtered off, immersed in an aqueous solution of bismuth acetate and ferric nitrate, and again reduced with a reducing agent as desired to precipitate the metals, followed by filtration and drying in vacuo. The thus prepared catalyst can be activated in the usual way.

In the present invention, an aldehyde and an alcohol are reacted in liquid phase in the presence of molecular oxygen by using the thus prepared catalyst to produce a corresponding carboxylic acid ester. In the following, a process for producing a carboxylic acid ester according to the present invention is illustrated.

The aldehydes usable as a starting material include saturated aldehydes such as acetaldehyde, propionaldehyde and isobutyl aldehyde, etc., unsaturated aldehydes such as acrolein, methacrolein and crotonaldehyde, etc. and aromatic aldehydes such as benzaldehyde and p-tolualdehyde, etc. Methacrolein, acrolein and their mixtures are important as the starting materials in production of methacrylic esters and acrylic esters of high industrial value. The alcohols usable as another starting material in the present invention include methanol, ethanol, isopropanol, allyl alcohol, methallyl alcohol and the like.

The aldehyde to alcohol ratio (by mole) in the reaction is preferably 1:100~1:1, more preferably 1:80~1:3.

The reaction may be batchwise, semi-batchwise or continuous. The catalyst is used in the state of being suspended in the reaction solution. The amount of the catalyst used is not specified, but in the case of batchwise reaction, the catalyst is preferably used in an amount of 0.1–20 parts by weight, more preferably 0.2–15 parts by weight per 100 parts by weight of the starting aldehyde. As the supply source of molecular oxygen, there can be used, beside oxygen itself, air, oxygen-enriched air and such. Molecular oxygen is usually supplied by blowing a gas such as air bubbling into the reaction solution. Hydrogen peroxide may be allowed to exist as an oxidizer in the reaction solution.

The reaction is carried out in the temperature range of 0°–100° C., preferably 30°–80° C. Usually the reaction is carried out under normal pressure, but it may be performed under pressure or under reduced pressure. A polymerization inhibitor such as hydroquinone or p-methoxyphenol may be added as desired to the reaction solution.

The catalyst used under these reaction conditions gradually decreases in activity in use. Therefore, the yield of the carboxylic acid ester produced with the catalyst used repeatedly for batchwise reactions or used for a long time for continuous reactions is greatly reduced.

According to the present invention, the catalyst which has decreased in activity in use can be regenerated by treating it in the presence of a reducing agent. The regeneration method for the deactivated catalyst is explained below.

As the reducing agent, at least one member selected from the group consisting of methanol, ethanol, formalin, acetaldehyde, propionaldehyde, isobutylaldehyde, acrolein, methacrolein and hydrazine is used. The amount of the reducing agent used for the regeneration treatment is not restricted, but it is usually 1–5,000 parts by weight, preferably 10–4,000 parts by weight, per 100 parts by weight of palladium in the catalyst.

The regeneration for the catalyst is carried out by suspending the catalyst in a liquid phase containing the reducing agent, and treating the suspension at 0°–100° C., preferably 20°–80° C., for 0.1–50 hours, preferably 0.5–40 hours. The treatment can be carried out under normal pressure, but it may also be performed under pressure or under reduced pressure. The treatment may be batchwise, semi-batchwise or continuous. If necessary it may be carried out under an atmosphere of at least one type of gas selected from the group consisting of nitrogen, carbon dioxide, helium and argon.

The regeneration treatment may be carried out in the reactor used for producing a carboxylic acid ester or outside the reactor after recovering the catalyst from the reactor. In case of performing the regeneration treatment in the reactor, it is possible to restore the catalyst activity by the simple operation of merely adding a reducing agent after completion of the carboxylic acid ester forming reaction. In case the unreacted material already existing in the reaction solution after the end of the reaction is the reducing agent itself, there is no need of adding any extra reducing agent since such unreacted material can be utilized as the reducing agent.

The present invention is further illustrated by the following examples, referential examples and comparative examples. In the experimental formula of the catalyst, the superscript to the right of each elemental symbol indicates parts by weight of the element supported on 100 parts by weight of the carrier, and the compound after the slash (/) indicates the carrier. Analyses were made by gas chromatography. In the table (Table 1), "Conversion (%)" and "Selectivity (%)" indicate conversion (%) of methacrolein and selectivity (%) of methyl methacrylate, respectively, unless otherwise noted.

EXAMPLE 1

Ten (10) grams of calcium carbonate was added to a solution of 1.40 g of tetraamminepalladium nitrate in 20 ml of pure water, and the mixture was refluxed with stirring for one hour. After dehydrating the mixture, 20 ml of a formalin solution was added to the mixture followed by filtration and washing with water to obtain a solid matter. This solid matter was added to a solution of 0.46 g of bismuth nitrate and 0.72 g of ferric nitrate in 40 ml of 3% dilute nitric acid and mixed at 60° C. for one hour. To this mixture was added 10 ml of a formalin solution, and the solution was filtered, washed with water and dried to obtain a catalyst of the following composition:

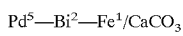

$Pd^5$—$Bi^2$—$Fe^1$/$CaCO_3$

Two (2.0) grams of this catalyst, 3.5 g of methacrolein and 80 g of methanol were supplied into a 200 ml flask having a reflux condenser. Further, a 0.03N (mol/dm$^3$) methanol solution of NaOH was added to the reaction solution to make its pH 10.5, and air was blown bubbling into the solution at a rate of 100 ml/min to carry out the reaction at a bath temperature of 70° C. for 4 hours to synthesize methyl methacrylate. An analysis of the collected reaction product showed 75.8% conversion of methacrolein and 97.3% selectivity of methyl methacrylate.

EXAMPLE 2

Ten (10) grams of $Pd^5$—$Bi^2$/$CaCO_3$ (produced by N.E. Chemcat Inc.) were added to a solution of 0.34 g of zinc acetate in 20 ml of water and mixed at 60° C. for one hour. To this mixture was added 5 ml of a formalin solution, and the solution was filtered, washed with water and dried to obtain a catalyst of the following composition:

$Pd^5$—$Bi^2$—$Zn^1$/$CaCO_3$

Using this catalyst, methyl methacrylate was synthesized by following the same procedure as in Example 1. The analytical result of the product is shown in Table 1.

EXAMPLE 3

The catalyst preparation process of Example 2 was followed except for use of 0.19 g of barium acetate in place of zinc acetate to obtain a catalyst of the following composition:

$Pd^5$—$Bi^2$—$Ba^1$/$CaCO_3$

Using this catalyst, methyl methacrylate was synthesized by following the same procedure as in Example 1. The analytical result of the product is shown in Table 1.

EXAMPLE 4

The catalyst preparation process of Example 2 was followed except for use of 0.14 g of germanium oxide in place of zinc acetate to obtain a catalyst of the following composition:

$Pd^5$—$Bi^2$—$Ge^1$/$CaCO_3$

Using this catalyst, methyl methacrylate was synthesized by following the same procedure as in Example 1. The analytical result of the product is shown in Table 1.

EXAMPLE 5

Methyl methacrylate was synthesized according to the same procedure as in Example 1 except that the amount of the catalyst prepared in Example 1 was increased to 3.5 g. The analytical result of the product is shown in Table 1.

EXAMPLE 6

Four (4.0) grams of the catalyst prepared in Example 1, 7.0 g of methacrolein and 80 g of methanol were supplied into a 200 ml flask having a reflux condenser. Further, a 0.03N (mol/dm$^3$) methanol solution of NaOH was added to the reaction solution to make its pH 10.5, and air was blown bubbling into the solution at a rate of 200 ml/min to carry out the reaction at a bath temperature of 70° C. for 4 hours to synthesize methyl methacrylate. An analysis of the collected reaction product showed 73.0% conversion of methacrolein and 96.8% selectivity of methyl methacrylate.

EXAMPLE 7

Using the catalyst of Example 1, methyl methacrylate was synthesized according to the same procedure as in Example 1 except that the reaction bath temperature was adjusted to 40° C. The analytical result of the product is shown in Table 1.

EXAMPLE 8

Using the catalyst of Example 1, methyl methacrylate was synthesized according to the same procedure as in Example 1 except that the reaction bath temperature was adjusted to 55° C. The analytical result of the product is shown in Table 1.

EXAMPLE 9

The catalyst preparation process of Example 1 was followed except that the amount of bismuth nitrate was 0.70 g to obtain a catalyst of the following composition:

$Pd^5$—$Bi^3$—$Fe^1$/$CaCO_3$

Using this catalyst, methyl methacrylate was synthesized according to the same procedure as in Example 1. The analytical result of the product is shown in Table 1.

EXAMPLE 10

The catalyst preparation process of Example 1 was followed except that the amounts of tetraamminepalladium nitrate and bismuth nitrate were changed to 2.81 g and 0.93 g, respectively, to obtain a catalyst of the following composition:

$Pd^{10}$—$Bi^4$—$Fe^1$/$CaCO_3$

Using this catalyst, methyl methacrylate was synthesized according to the same procedure as in Example 1. The analytical result of the product is shown in Table 1.

EXAMPLE 11

Using the catalyst of Example 3, methyl acrylate was synthesized according to same procedure as in Example 3 except for use of 2.80 g of acrolein in place of methacrolein. The analytical result of the product is shown in Table 1. In the table, conversion is that of acrolein and selectivity is that of methyl acrylate.

EXAMPLE 12

The catalyst preparation process of Example 1 was followed except that a solution of 0.46 g of bismuth nitrate, 0.18 g of lead acetate and 0.72 g of ferric nitrate in 40 ml of 3% dilute nitric acid was used in place of a solution of 0.46 g of bismuth nitrate and 0.72 g of ferric acetate in 40 ml of 3% dilute nitric acid, and that the amount of the formalin solution was increased to 15 ml to obtain a catalyst of the following composition:

$Pd^5$—$Bi^2$—$Pb^1$—$Fe^1$/$CaCO_3$

Using this catalyst, methyl methacrylate was synthesized according to the same procedure as in Example 1. The analytical result of the product is shown in Table 1.

EXAMPLE 13

The catalyst preparation process of Example 2 was followed except that a solution of 0.34 g of zinc acetate and 0.18 g of lead acetate in 50 ml of water was used in place of a solution of 0.34 g of zinc acetate in 20 ml of water, and that the amount of the formalin solution was increased to 10 ml to obtain a catalyst of the following composition:

$Pd^5$—$Bi^2$—$Pb^1$—$Zn^1$/$CaCO_3$

Using this catalyst, methyl methacrylate was synthesized according to the same procedure as in Example 1. The analytical result of the product is shown in Table 1.

EXAMPLE 14

The catalyst preparation process of Example 3 was followed except for use of 0.32 g of lead nitrate in place of lead acetate to obtain a catalyst of the following composition:

Pd$^5$—Bi$^2$—Pb$^2$—Zn$^1$/CaCO$_3$

Using this catalyst, methyl methacrylate was synthesized according to the same procedure as in Example 1. The analytical result of the product is shown in Table 1.

EXAMPLE 15

The catalyst preparation process of Example 13 was followed except for use of 0.19 g of barium acetate in place of zinc acetate and 0.16 g of lead nitrate in place of lead acetate to obtain a catalyst of the following composition:

Pd$^5$—Bi$^2$—Pb$^1$—Ba$^1$/CaCO$_3$

Using this catalyst, methyl methacrylate was synthesized according to the same procedure as in Example 1. The analytical result of the product is shown in Table 1.

EXAMPLE 16

The catalyst preparation process of Example 13 was followed except for use of 0.14 g of germanium oxide in place of zinc acetate to obtain a catalyst of the following composition:

Pd$^5$—Bi$^2$—Pb$^1$—Ge$^1$/CaCO$_3$

Using this catalyst, methyl methacrylate was synthesized according to the same procedure as in Example 1. The analytical result of the product is shown in Table 1.

EXAMPLE 17

Methyl methacrylate was synthesized according to the same procedure as in Example 1 except that the amount of the catalyst prepared in Example 12 was increased to 4.0 g. The analytical result of the product is shown in Table 1.

EXAMPLE 18

Four (4.0) grams of the catalyst prepared in Example 12, 7.0 g of methacrolein and 80 g of methanol were supplied into a 200 ml flask having a reflux condenser. Further, a 0.03N (mol/dm$^3$) methanol solution of NaOH was added to the reaction solution to make its pH 10.5, and air was blown bubbling into the solution at a rate of 200 ml/min to carry out the reaction at a bath temperature of 70° C. for 4 hours to synthesize methyl methacrylate. The analytical result of the product is shown in Table 1.

EXAMPLE 19

Methyl methacrylate was synthesized according to the same procudure as in Example 1 except that the catalyst of Example 12 was used and the reaction bath temperature was set at 40° C. The analytical result of the product is shown in Table 1.

EXAMPLE 20

Methyl methacrylate was synthesized according to the same procedure as in Example 1 except that the catalyst of Example 12 was used and the reaction bath temperature was set at 55° C. The analytical result of the product is shown in Table 1.

EXAMPLE 21

The catalyst preparation process of Example 12 was followed except that the amount of bismuth nitrate was changed to 0.70 g to obtain a catalyst of the following composition:

Pd$^5$—Bi$^3$—Pb$^1$—Fe$^1$/CaCO$_3$

Using this catalyst, methyl methacrylate was synthesized according to the same procedure as in Example 1. The analytical result of the product is shown in Table 1.

EXAMPLE 22

The catalyst preparation process of Example 12 was followed except that the amounts of tetraamminepalladium nitrate and bismuth nitrate were made 2.81 g and 0.93 g, respectively, to obtain a catalyst of the following composition:

Pd$^{10}$—Bi$^4$—Pb$^1$—Fe$^1$/CaCO$_3$

Using this catalyst, methyl methacrylate was synthesized according to the same procedure as in Example 1. The analytical result of the product is shown in Table 1.

EXAMPLE 23

Using the catalyst of Example 16, methyl acrylate was synthesized according to the same procedure as in Example 16 except for use of 2.80 g of acrolein in place of methacrolein. The analytical result of the product is shown in Table 1. In the table, conversion is that of acrolein and selectivity is that of methyl acrylate.

EXAMPLE 24

Ten (10) grams of calcium carbonate was added to a solution of 1.40 g of tetraamminepalladium nitrate in 20 ml of pure water, and the mixture was refluxed with stirring for one hour. After dehydrating the mixture, 20 ml of a formalin solution was added to the mixture followed by filtration and washing with water obtain a solid matter. This solid matter was added to a solution of 0.18 g of lead acetate and 0.72 g of ferric nitrate in 40 ml of pure water and mixed at 60° C. for one hour. To this mixture was added 15 ml of a formalin solution, and the solution was filtered, washed with water and dried to obtain a catalyst of the following composition:

Pd$^5$—Pb$^1$—Fe$^1$/CaCO$_3$

Using this catalyst, methyl methacrylate was synthesized according to the same procedure as in Example 1. The analytical result of the product is shown in Table 1.

EXAMPLE 25

The catalyst preparation process of Example 24 was followed except for use of 0.77 g of chromium nitrate in place of ferric nitrate to obtain a catalyst of the following composition:

Pd$^5$—Pb$^1$—Cr$^1$/CaCO$_3$

Using this catalyst, methyl methacrylate was synthesized according to the same procedure as in Example 1. The analytical result of the product is shown in Table 1.

EXAMPLE 26

The catalyst preparation process of Example 24 was followed except for use of 0.42 g of cobalt acetate in place of ferric nitrate to obtain a catalyst of the following composition:

Pd$^5$—Pb$^1$—Co$^1$/CaCO$_3$

Using this catalyst, methyl methacrylate was synthesized according to the same procedure as in Example 1. The analytical result of the product is shown in Table 1.

EXAMPLE 27

The catalyst preparation process of Example 24 was followed except for use of 0.34 g of zinc acetate in place of ferric nitrate to obtain a catalyst of the following composition:

$$Pd^5\text{—}Pb^1\text{—}Zn^1/CaCO_3$$

Using this catalyst, methyl methacrylate was synthesized according to the same procedure as in Example 1. The analytical result of the product is shown in Table 1.

EXAMPLE 28

The catalyst preparation process of Example 24 was followed except for use of 0.16 g of silver acetate in place of ferric nitrate to obtain a catalyst of the following composition:

$$Pd^5\text{—}Pb^1\text{—}Ag^1/CaCO_3$$

Using this catalyst, methyl methacrylate was synthesized according to the same procedure as in Example 1. The analytical result of the product is shown in Table 1.

EXAMPLE 29

Ten (10) grams of $Pd^5$—$Pb^1/CaCO_3$ (produced by N.E. Chemcat Inc.) was added to a solution of 0.72 g of ferric nitrate and 0.17 g of zinc acetate in 50 ml of water and mixed at 60° C. for one hour. To this mixture was added 15 ml of a formalin solution, and the solution was filtered, washed with water and dried to obtain a catalyst of the following composition:

$$Pd^5\text{—}Pb^1\text{—}Fe^1\text{—}Zn^{0.5}/CaCO_3$$

Using this catalyst, methyl methacrylate was synthesized according to the same procedure as in Example 1. The analytical result of the product is shown in Table 1.

EXAMPLE 30

Methyl methacrylate was synthesized according to the same procedure as in Example 1 except that the amount of the catalyst prepared in Example 24 was increased to 4.0 g. The analytical result of the product is shown in Table 1.

EXAMPLE 31

Four (4.0) grams of the catalyst prepared in Example 24, 7.0 g of methacrolein and 80 g of methanol were supplied into a 200 ml flask having a reflux condenser. Further, a 0.03N (mol/dm³) methanol solution of NaOH was added to the reaction solution to make its pH 10.5, and air was blown bubbling into the solution at a rate of 200 ml/min to carry out the reaction at a bath temperature of 70° C. for 4 hours to synthesize methyl methacrylate. An analysis of the collected reaction product showed 79.8% conversion of methacrolein and 94.5% selectivity of methyl methacrylate.

EXAMPLE 32

Methyl methacrylate was synthesized according to the same procedure as in Example 1 except that the catalyst of Example 24 was used and the reaction bath temperature was set at 40° C. The analytical result of the product is shown in Table 1.

EXAMPLE 33

Methyl methacrylate was synthesized according to the same procedure as in Example 1 except that the catalyst of Example 24 was used and the reaction bath temperature was set at 55° C. The analytical result of the product is shown in Table 1.

EXAMPLE 34

The catalyst preparation process of Example 24 was followed except that the amount of lead acetate was changed to 0.37 g to obtain a catalyst of the following composition:

$$Pd^5\text{—}Pb^2\text{—}Fe^1/CaCO_3$$

Using this catalyst, methyl methacrylate was synthesized according to the same procedure as in Example 1. The analytical result of the product is shown in Table 1.

EXAMPLE 35

Methyl acrylate was synthesized according to the same procedure as in Example 1 except for use of the catalyst of Example 24 and 2.80 g of acrolein in place of methacrolein. The analytical result of the product is shown in Table 1. In the table, conversion is that of acrolein and selectivity is that of methyl acrylate.

EXAMPLE 36

Ten (10) grams of zinc oxide was added to a solution of 1.40 g of tetraamminepalladium nitrate in 20 ml of pure water, and the mixture was refluxed with stirring for one hour. After dehydrating the mixture, 20 ml of a formalin solution was added to the mixture followed by filtration and washing with water to obtain a solid matter. This solid matter was added to a solution of 0.46 g of bismuth nitrate and 0.18 g of lead acetate in 40 ml of 3% dilute nitric acid and mixed at 60° C. for one hour. To this mixture was added 15 ml of a formalin solution, and the solution was filtered, washed with water and dried to obtain a catalyst of the following composition:

$$Pd^5\text{—}Bi^2\text{—}Pb^1/ZnO$$

Using this catalyst, methyl methacrylate was synthesized according to the same procedure as in Example 1. The analytical result of the product is shown in Table 1.

EXAMPLE 37

The catalyst preparation process of Example 36 was followed except for use of 0.32 g of lead nitrate in place of lead acetate to obtain a catalyst of the following composition:

$$Pd^5\text{—}Bi^2\text{—}Pb^2/ZnO$$

Using this catalyst, methyl methacrylate was synthesized according to the same procedure as in Example 1. The analytical result of the product is shown in Table 1.

EXAMPLE 38

The catalyst preparation process of Example 36 was followed except for use of 0.72 g of ferric nitrate in place of lead acetate to obtain a catalyst of the following composition:

$$Pd^5\text{—}Bi^2\text{—}Fe^1/ZnO$$

Using this catalyst, methyl methacrylate was synthesized according to the same procedure as in Example 1. The analytical result of the product is shown in Table 1.

EXAMPLE 39

The catalyst preparation process of Example 36 was followed except for use of 0.45 g of manganese acetate in place of lead acetate to obtain a catalyst of the following composition:

$$Pd^5\text{—}Bi^2\text{—}Mn^1/ZnO$$

Using this catalyst, methyl methacrylate was synthesized according to the same procedure as in Example 1. The analytical result of the product is shown in Table 1.

EXAMPLE 40

The catalyst preparation process of Example 36 was followed except for use of 0.42 g of cobalt acetate in place of lead acetate to obtain a catalyst of the following composition:

$$Pd^5\text{—}Bi^2\text{—}Co^1/ZnO$$

Using this catalyst, methyl methacrylate was synthesized according to the same procedure as in Example 1. The analytical result of the product is shown in Table 1.

EXAMPLE 41

The catalyst preparation process of Example 36 was followed except for use of 0.50 g of nickel nitrate in place of lead acetate to obtain a catalyst of the following composition:

$$Pd^5\text{—}Bi^2\text{—}Ni^1/ZnO$$

Using this catalyst, methyl methacrylate was synthesized according to the same procedure as in Example 1. The analytical result of the product is shown in Table 1.

EXAMPLE 42

The catalyst preparation process of Example 36 was followed except for use of 0.39 g of cuprous sulfate in place of lead acetate to obtain a catalyst of the following composition:

$$Pd^5\text{—}Bi^2\text{—}Cu^1/ZnO$$

Using this catalyst, methyl methacrylate was synthesized according to the same procedure as in Example 1. The analytical result of the product is shown in Table 1.

EXAMPLE 43

The catalyst preparation process of Example 36 was followed except for use of 0.34 g of zinc acetate in place of lead acetate to obtain a catalyst of the following composition:

$$Pd^5\text{—}Bi^2\text{—}Zn^1/ZnO$$

Using this catalyst, methyl methacrylate was synthesized according to the same procedure as in Example 1. The analytical result of the product is shown in Table 1.

EXAMPLE 44

The catalyst preparation process of Example 36 was followed except for use of 0.14 g of germanium dioxide in place of lead acetate to obtain a catalyst of the following composition:

$$Pd^5\text{—}Bi^2\text{—}Ge^1/ZnO$$

Using this catalyst, methyl methacrylate was synthesized according to the same procedure as in Example 1. The analytical result of the product is shown in Table 1.

EXAMPLE 45

The catalyst preparation process of Example 36 was followed except for use of 0.19 g of barium acetate in place of lead acetate to obtain a catalyst of the following composition:

$$Pd^5\text{—}Bi^2\text{—}Ba^1/ZnO$$

Using this catalyst, methyl methacrylate was synthesized according to the same procedure as in Example 1. The analytical result of the product is shown in Table 1.

EXAMPLE 46

The catalyst preparation process of Example 36 was followed except for use of 0.18 g of telluric acid in place of lead acetate to obtain a catalyst of the following composition:

$$Pd^5\text{—}Bi^2\text{—}Te^1/ZnO$$

Using this catalyst, methyl methacrylate was synthesized according to the same procedure as in Example 1. The analytical result of the product is shown in Table 1.

EXAMPLE 47

Methyl methacrylate was synthesized according to the same proceddure as in Example 1 except that the amount of the catalyst prepared in Example 36 was increased to 4.0 g. The analytical result of the product is shown in Table 1.

EXAMPLE 48

Four (4.0) grams of the catalyst prepared in Example 36, 7.0 g of methacrolein and 80 g of methanol were supplied into a 200 ml flask having a reflux condenser. Further, a 0.03N (mol/dm$^3$) methanol solution of NaOH was added to the reaction solution to make its pH 10.5, and air was blown bubbling into the solution at a rate of 200 ml/min to carry out the reaction at a bath temperature of 70° C. for 4 hours to synthesize methyl methacrylate. The analytical result of the product is shown in Table 1.

EXAMPLE 49

Methyl methacrylate was synthesized according to the same procedure as in Example 1 except that the catalyst of Example 36 was used and the reaction bath temperature was set at 40° C. The analytical result of the product is shown in Table 1.

EXAMPLE 50

Methyl methacrylate was synthesized according to the same procedure as in Example 1 except that the catalyst of Example 36 was used and the reaction bath temperature was set at 55° C. The analytical result of the product is shown in Table 1.

EXAMPLE 51

The catalyst preparation process of Example 36 was followed except that the amount of bismuth nitrate was changed to 0.70 g to obtain a catalyst of the following composition:

$$Pd^5\text{—}Bi^3\text{—}Pb^1/ZnO$$

Using this catalyst, methyl methacrylate was synthesized according to the same procedure as in Example 1. The analytical result of the product is shown in Table 1.

EXAMPLE 52

Ten (10) grams of zinc oxide was added to a solution of 1.40 g of tetraamminepalladium nitrate in 20 ml of pure water, and the mixture was refluxed with stirring for one hour. After dehydrating the mixture, 20 ml of a formalin solution was added thereto, followed by filtration and washing with water to obtain a solid matter. This solid matter was added to a solution of 0.46 g of bismuth nitrate, 0.18 g of lead acetate and 0.72 g of ferric nitrate in 60 ml of 3% dilute nitric acid and mixed at 60° C. for one hour. To this mixture was added 15 ml of a formalin solution, and the solution was filtered, washed with water and dried to obtain a catalyst of the following composition:

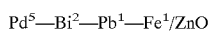

$Pd^5$—$Bi^2$—$Pb^1$—$Fe^1$/ZnO

Using this catalyst, methyl methacrylate was synthesized according to the same procedure as in Example 1. The analytical result of the product is shown in Table 1.

EXAMPLE 53

Methyl acrylate was synthesized according to the same procedure as in Example 36 except for use of 2.80 g of acrolein in place of methacrolein. The analytical result of the product is shown in Table 1. In the table, conversion is that of acrolein and selectivity is that of methyl acrylate.

REFERENTIAL EXAMPLE 1

Ten (10) grams of calcium carbonate was added to a solution of 1.40 g of tetraamminepalladium nitrate in 20 ml of pure water, and the mixture was refluxed with stirring for one hour. After dehydrating the mixture, 20 ml of a formalin solution was added, followed by filtration of the solution and washing with water to obtain a solid matter. This solid matter was added to a solution of 0.46 g of bismuth nitrate and 0.19 g of barium acetate in 40 ml of 3% dilute nitric acid and mixed at 60° C. for one hour. To this mixture was added 10 ml of a formalin solution, and the solution was filtered, washed with water and dried to obtain a catalyst of the following composition:

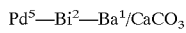

$Pd^5$—$Bi^2$—$Ba^1$/$CaCO_3$

Two (2.0) grams of the above catalyst, 3.5 g of methacrolein and 80 g of methanol were supplied into a 200 ml flask having a reflux condenser. Further, a 0.03N (mol/dm³) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 73.3% conversion of methacrolein and 96.0% selectivity of methyl methacrylate. When the catalyst was further used repeatedly for the reaction under the same conditions for a long time, methacrolein conversion dropped to 56.3% while methyl methacrylate selectivity lowered to 89.1%.

EXAMPLE 54

To 2.0 g of a catalyst which had decreased in activity after long-time repeated use for the reactions of Referential Example 1 and which was contained in a 200 ml flask having a reflux condenser, 80 g of methanol was added and the solution was treated with stirring at a bath temperature of 70° C. for one hour while blowing nitrogen into the solution at a rate of 10 ml/min. After cooling, 3.5 g of methacrolein was further added and the mixture was reacted under the same conditions as in Referential Example 1. Methacrolein conversion was 73.3% and methyl methacrylate selectivity was 96.6%.

EXAMPLE 55

Two (2.0) grams of the catalyst recovered after long-time repeated use for the reaction of Referential Example 1 with its activity reduced was supplied into a 200 ml flask having a reflux condenser. Ten ml of a formalin solution was added to the catalyst and treated with stirring in a nitrogen atmosphere at 30° C. for one hour. Then the solution was filtered, washed with water and dried to obtain a regenerated catalyst.

Two (2.0) grams of this regenerated catalyst, 3.5 g of methacrolein and 80 g of methanol were supplied into a 200 ml flask having a reflux condenser. Then a 0.03N (mol/dm³) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 73.1% conversion of methacrolein and 96.2% selectivity of methyl methacrylate.

EXAMPLE 56

Catalyst regeneration and reaction with the regenerated catalyst were carried out according to the same procedures as in Example 55 except that 10 ml of an acetaldehyde solution was used instead of 10 ml of a formalin solution, and that the treatment was carried out at 20° C. for 2 hours. Methacrolein conversion was 72.9% and methyl methacrylate selectivity was 95.7%.

EXAMPLE 57

Catalyst regeneration and reaction with the regenerated catalyst were carried out according to the same procedures as in Example 55 except that a mixture of 1 g of methacrolein and 50 g of methanol was used instead of 10 ml of a formalin solution, and that the treatment was carried out in an air atmosphere at 40° C. for one hour. Methacrolein conversion was 73.5% and methyl methacrylate selectivity was 95.9%.

EXAMPLE 58

Catalyst regeneration and reaction with the regenerated catalyst were carried out according to the same procedures as in Example 55 except that 20 ml of ethanol was used instead of 10 ml of a formalin solution, and that the treatment was carried out at a bath temperature of 70° C. for one hour while blowing a 1:1 (by volume) nitrogen/carbon dioxide mixed gas into the solution at a rate of 10 ml/min. Methacrolein convernsion was 73.5% and methyl methacrylate selectivity was 96.1%.

EXAMPLE 59

Catalyst regeneration and reaction with the regenerated catalyst were carried out according to the same procedures as in Example 55 except that 10 ml of a hydrazine solution was used instead of 10 ml of a formalin solution, and that the treatment was carried out in a carbon dioxide gas atmosphere at 40° C. for one hour. Methacrolein conversion was 73.8% and methyl methacrylate selectivity was 96.4%.

EXAMPLE 60

Catalyst regeneration and reaction with the regenerated catalyst were carried out according to the same procedures as in Example 55 except that 10 ml of isobutylaldehyde was used instead of 10 ml of a formalin solution, and that the treatment was carried out in a helium atmosphere at 40° C. for one hour. Methacrolein conversion was 72.0% and methyl methacrylate selectivity was 96.1%.

EXAMPLE 61

Catalyst regeneration and reaction with the regenerated catalyst were carried out according to the same procedures as in Example 55 except that a mixed solution of 1 g of acrolein and 30 g of methanol was used instead of 10 ml of formalin solution, and that the treatment was carried out in an air atmosphere at 40° C. for one hour. Methacrolein convernsion was 72.5% and methyl methacrylate selectivity was 95.5%.

REFERENTIAL EXAMPLE 2

A solution of 1.40 g of tetraamminepalladium nitrate in 20 ml of pure water was supplied into a 200 ml flask having a reflux condenser, to which 10 g of zinc oxide was added and the mixture was refluxed with stirring. After deydrating the mixture, 20 ml of a formalin solution was added thereto followed by filtration and washing with water to obtain a solid matter. This solid matter was added to a solution of 0.46 g of bismuth nitrate and 0.18 g of lead acetate in 40 ml of 3% dilute nitric acid and mixed at 60° C. for one hour. To this mixture was added 15 ml of a formalin solution, and the solution was filtered, washed with water and dried to obtain a catalyst of the following composition:

$Pd^5$—$Bi^2$—$Pb^1$/ZnO

Using this catalyst, the reaction of Referential Example 1 was carried out, with the result of 76.9% conversion of methacrolein and 96.8% selectivity of methyl methacrylate. When the catalyst was further used repeatedly for the reaction under the same conditions for a long time, methacrolein convernsion dropped to 62.8% while methyl methacrylate selectivity lowered to 87.6%.

EXAMPLE 62

To 2.0 g of the catalyst which had decreased in activity after long-time repeated use for the reaction of Referential Example 2 and which was contained in a 200 ml flask having a reflux condenser, 80 g of methanol was added and the solution was treated with stirring at a bath temperature of 50° C. for one hour while blowing nitrogen into the solution at a rate of 10 ml/min. After cooling, 3.5 g of methacrolein was further added and the mixture was reacted under the same conditions as in Referential Example 1. Methacrolein convernsion was 77.3% and methyl methacrylate selectivity was 96.7%.

EXAMPLE 63

Two (2.0) grams of the catalyst recovered after long-time repeated use for the reaction of Referential Example 2 with its activity reduced was supplied into a 200 ml flask having a reflux condenser. Ten (10) milliliters of hydrazine solution was added to the catalyst and treated with stirring in an argon gas atmosphere at 40° C. for one hour, and the solution was filtered, washed with water and dried to obtain a regenerated catalyst.

Two (2.0) grams of this regenerated catalyst, 3.5 g of methacrolein and 80 g of methanol were supplied into a 200 ml flask having a reflux condenser. Then a 0.03N ($mol/dm^3$) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction produc tshowed 76.7% conversion of methacrolein and 96.5% selectivity of methyl methacrylate.

REFERENTIAL EXAMPLE 3

Ten g of $Pd^5$—$Pb^1$/$CaCO_3$ (produced by N.E. Chemcat Inc.) was added to a solution of 0.34 g of zinc acetate in 50 ml of pure water and mixed at 60° C. for one hour. To this mixture was added 10 ml of a formalin solution, and the solution was filtered, washed with water and dried to obtain a catalyst of the following composition:

$Pd^5$—$Pb^1$—$Zn^1$/$CaCO_3$

When this catalyst was used for the reaction of Referential Example 2, methacrolein conversion was 80.6% and methyl methacrylate selectivity was 95.3%. When the catalyst was further used repeatedly for the same reaction for a long time continuously, methacrolein conversion dropped to 66.4% while methyl methacrylate selectivity lowered to 89.7%.

EXAMPLE 64

To 2.0 g of the catalyst which had decreased in activity after long-time repeated used for the reaction of Referential Example 3 and which was contained in a 200 ml flask having a reflux condenser, 80 g of methanol was added and the solution was treated with stirring at a bath temperature of 40° C. for one hour while blowing nitrogen into the solution at a rate of 20 ml/min. After cooling, 3.5 g of methacrolein was added and the mixture was reacted under the same conditions as in Referential Example 1. Methacrolein conversion was 80.7% and methyl methacrylate selectivity was 95.0%.

EXAMPLE 65

Two (2.0) grams of the catalyst recovered after long-time repeated use for the reaction of Referential Example 3 with its activity decreased was supplied into a 200 ml flask havig a reflux condenser. Ten ml of a formalin solution was added to the catalyst and treated with stirring in a nitrogen atmosphere at 30° C. for one hour, and the solution was filtered, washed with water and dried to obtain a regenerated catalyst.

Two (2.0) grams of this regenerated catalyst, 3.5 g of methacrolein and 80 g of methanol were supplied into a 200 ml flask having a reflux condenser. Then a 0.03N ($mol/dm^3$) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 80.5% conversion of methacrolein and 95.6% selectivity of methyl methacrylate.

REFERENTIAL EXAMPLE 4

Ten (10) grams of calcium carbonate was added to a solution of 1.40 g of tetraamminepalladium nitrate in 20 ml of pure water, and the mixture was refluxed with stirring. After dehydrating the mixture, 20 ml of a formalin solution was added thereto followed by filtration and washing with water to obtain a solid matter. This solid matter was added to a solution of 0.46 g of bismuth nitrate and 0.72 g of ferric nitrate in 40 ml of 3% dilute nitric acid and mixed at 60° C. for one hour. To this mixture was added 10 ml of a formalin solution, and the solution was filtered, washed with water and dried to obtain a catalyst of the following composition:

$Pd^5$—$Bi^2$—$Fe^1$/$CaCO_3$

When the reaction of Referential Example 1 was carried out by using this catalyst, methacrolein conversion 75.8% and methyl methacrylate selectivity was 97.3%. When the catalyst was further used repeatedly for the same reaction for a long time continuously, methacrolein conversion dropped to 60.5% while methyl methacrylate selectivity lowered to 92.7%.

EXAMPLE 66

To 2.0 g of the catalyst which had decreased in activity after long-time repeated use for the reaction of Referential Example 4 and which was contained in a 200 ml flask having a reflux condenser, 80 g of methanol was added and the solution was treated with stirring at a bath temperature of 70° C. for one hour while blowing nitrogen into the solution at a rate of 20 ml/min. After cooling, 3.5 g of methacrolein was further added and the mixture was reacted under the same conditions as in Referential Example 1. Methacrolein conversion was 75.6% and methyl methacrylate selectivity was 97.5%.

EXAMPLE 67

Two (2.0) grams of the catalyst recovered after long-time repeated use for the reaction of Referential Example 4 with its activity decreased was supplied into a 200 ml flask having a reflux condenser. Ten ml of a formalin solution was added to the catalyst and treated with stirring in a nitrogen atmosphere at 30° C. for one hour, and the solution was filtered, washed with water and dried to obtain a regenerated catalyst.

Two (2.0) grams of this regenerated catalyst, 3.5 g of methacrolein amd 80 g of methanol were supplied into a 200 ml flask having a reflux condenser. Then a 0.03N (mol/dm$^3$) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 75.1% convernsion of methacrolein and 97.3% selectivity of methyl methacrylate.

REFERENTIAL EXAMPLE 5

Ten (10) grams of $Pd^5$—$Pb^1$/$CaCO_3$ (produced by N.E. Chemcat Inc.) was added to a solution of 0.34 g of zinc acetate and 0.72 g of ferric nitrate in 70 ml of pure water and mixed at 60° C. for one hour. To this mixture was added 20 ml of a formalin solution, and the solution was filtered, washed with water and dried to obtain a catalyst of the following composition:

$Pd^5$—$Pb^1$—$Fe^1$—$Zn^1$/$CaCO_3$

When this catalyst was used for the reaction of Referential Example 1, methacrolein conversion was 83.5% and methyl methacrylate selectivity was 95.0%. When the catalyst was further used repeatedly for the same reaction for a long time continuously, methacrolein conversion dropped to 68.3% while methyl methacrylate selectivity lowered to 90.1%.

EXAMPLE 68

To 2.0 g of the catalyst which had decreased in activity after long-time repeated use for the reaction of Referential Example 5 and which was contained in a 200 ml flask having a reflux condenser, 80 g of methanol was added and the solution was treated with stirring at a bath temperature of 50° C. for one hour while blowing nitrogen into the solution at a rate of 20 ml/min. After cooling, 3.5 g of methacrolein was further added and the mixture was reacted under the same conditions as in Referential Example 1. Methacrolein conversion was 84.0% and methyl methacrylate selectivity was 94.5%.

EXAMPLE 69

Two (2.0) grams of the catalyst recovered after long-time repeated use for the reaction of Referential Example 5 with its activity decreased was supplied into a 200 ml flask having a reflux condenser. Ten ml of a formalin solution was added to the catalyst and treated with stirring in a nitrogen atmosphere at 30° C. for one hour, and the solution was filtered, washed with water and dried to obtain a regenerated catalyst.

Two (2.0) grams of this regenerated catalyst, 3.5 g of methacrolein and 80 g of methanol were supplied into a 200 ml flask having a reflux condenser. Then a 0.03N (mol/dm$^3$) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 83.3% conversion of methacrolein and 94.9% selectivity of methyl methacrylate.

REFERENTIAL EXAMPLE 6

Ten (10) grams of calcium carbonate was added to a solution of 1.40 g of tetraamminepalladium nitrate in 20 ml of pure water, and the mixture was refluxed with stirring. After dehydrating the mixture, 20 ml of a formalin solution was added thereto followed by filtration and washing with water to obtain a solid matter. This solid matter was added to a solution of 0.18 g of lead acetate and 0.72 g of ferric nitrate in 40 ml of pure water and mixed at 60° C. for one hour. To this mixture was added 15 ml of a formalin solution, and the solution was filtered, washed with water and dried to obtain a catalyst of the following composition:

$Pd^5$—$Pb^1$—$Fe^1$/$CaCO_3$

Two (2.0) grams of this catalyst, 2.8 g of acrolein and 80 g of methanol were supplied into a 200 ml flask having a reflux condenser. Then a 0.03N (mol/dm$^3$) methanol solution of NaOH was added to the reaction solution to make its pH 10.5, and air was blown bubbling into the solution at a rate of 100 ml/min to carry out the reaction at a bath temperature of 70° C. for 4 hours. An analysis of the collected reaction product showed 85.0% conversion of acrolein and 95.7% selectivity of methyl acrylate. When the catalyst was further used repeatedly for the same reaction for a long time continuously, acrolein conversion dropped to 69.9% while methyl acrylate selectivity lowered to 89.3%.

EXAMPLE 70

To 2.0 g of the catalyst which had decreased in activity after long-time repeated use for the reaction of Referenctial Example 6 and which was contained in a 200 ml flask having a reflux condenser, 80 g of methanol was added and the solution was treated with stirring at a bath temperature of 70° C. for one hour while blowing nitrogen into the solution at a rate of 20 ml/min. After cooling, 2.8 g of acrolein was added and the mixture was reacted under the same conditions as in Referential Example 1. Acrolein conversion was 85.3% and methyl acrylate selectivity was 95.5%.

EXAMPLE 71

Two (2.0) grams of the catalyst recovered after long-time repeated use for the reactio of Referential Example 6 with its activity decreased was supplied into a 200 ml flask having a reflux condenser. Ten ml of a formalin solution was added to the catalyst and stirred in a nitrogen atmosphere at 30° C. for one hour. Then the solution was filtered, washed with water and dried to obtain a regenerated catalyst.

Two (2.0) grams of this regenerated catalyst, 2.8 g of acrolein and 80 g of methanol were supplied into a 200 ml flask having a reflux condenser. Then a 0.03N (mol/dm$^3$) methanol solution of NaOH was added to the reaction solutionn to make its pH 10.5, and air was blown bubbling into the solution at a rate of 100 ml/min to carry out the reaction at a bath temperature of 70° C. for 4 hours. An analysis of the collected reaction product showed 84.9% conversion of acrolein and 95.6% selectivity of methyl acrylate.

COMPARATIVE EXAMPLE 1

Using $Pd^5$—$Bi^2$/$CaCO_3$ (produced by N.E. Chemcat Inc.), methyl methacrylate was synthesized according to the same procedure as in Example 1. The analytical result of the product is shown in Table 1.

COMPARATIVE EXAMPLE 2

The catalyst preparation process of Example 1 was followed except for use of magnesium oxide as carrier to obtain a catalyst of the following composition:

$Pd^5$—$Bi^2$—$Fe^1$/MgO

Using this catalyst, methyl methacrylate was synthesized according to the same procedure as in Example 1. The analytical result of the product is shown in Table 1. It is seen that use of magnesium oxide, which is generally considered as a synonym for carrier, resulted in a marked reduction of selectivity.

COMPARATIVE EXAMPLE 3

A zinc-free catalyst was prepared in the following way according to Example 13. Ten g of $Pd^5$—$Bi^2$/$CaCO_3$ (produced by N.E. Chemcat Inc.) was added to a solution of 0.18 g of lead acetate in 50 ml of water and mixed at 60° C. for one hour. To this mixture was added 10 ml of a formalin solution, and the solution was filtered, washed with water and dried to obtain a catalyst of the following composition:

$Pd^5$—$Bi^2$—$Pb^1$/$CaCO_3$

Using this catalyst, methyl methacrylate was synthesized according to the same procedure as in Example 1. The analytical result of the product is shown in Table 1.

COMPARATIVE EXAMPLE 4

The catalyst preparation procedure of Example 12 was followed except for use of magnesium oxide as carrier to obtain a catalyst of the following composition:

$Pd^5$—$Bi^2$—$Pb^1$—$Fe^1$/MgO

Using this catalyst, methyl methacrylate was synthesized according to the same procedure as in Example 1. The analytical result of the product is shown in Table 1. It is seen that in this case, too, selectivity was greatly reduced by use of magnesium oxide as carrier.

COMPARATIVE EXAMPLE 5

Using $Pd^5$—$Pb^1$/$CaCO_3$ (produced by N.E. Chemcat Inc.), methyl methacrylate was synthesized according to the same procedure as in Example 1. The analytical result of the product is shown in Table 1.

COMPARATIVE EXAMPLE 6

Using $Pd^5$—$Pb^1$—$Fe^1$/MgO, methyl methacrylate was synthesized according to the same procedure as in Example 1. The analytical result of the product is shown in Table 1. It is seen that selectivity was greatly reduced by use of magnesium oxide which is generally considered as a synonym for carrier.

COMPARATIVE EXAMPLE 7

Ten (10) grams of zinc oxide was added to a solution of 1.40 g of tetraamminepalladium nitrate in 20 ml of pure water and the mixture was refluxed with stirring for one hour. After dehydrating the mixture, 20 ml of a formalin solution was added thereto followed by filtration and washing with water to obtain a solid matter. This solid matter was added to a solution of 0.46 g of bismuth nitrate in 40 ml of 3% dilute nitric acid and mixed at 60° C. for one hour. To this mixture was added 15 ml of a formalin solution, and the solution was filtered, washed with water and dried to obtain a catalyst of the following composition:

$Pd^5$—$Bi^2$/ZnO

Using this catalyst, methyl methacrylate was synthesized according to the same procedure as in Example 1. The analytical result of the product is shown in Table 1. Selectivity lowered when using a catalyst having palladium and bismuth alone supported.

COMPARATIVE EXAMPLE 8

A catalyst of the following composition was prepared according to the procedure of Example 36:

$Pd^5$—$Bi^2$—$Pb^1$/MgO

Using this catalyst, methyl methacrylate was synthesized according to the same procedure as in Example 1. The analytical result of the product is shown in Table 1. It is seen that selectivity was greatly reduced when magnesium oxide was used as carrier.

COMPARATIVE EXAMPLE 9

A catalyst of the following composition was prepared according to the procedure of Example 36:

$Pd^5$—$Bi^2$—$Pb^1$/$ZrO_3$

Using this catalyst, methyl methacrylate was synthesized according to the same procedure as in Example 1. The analytical result of the product is shown in Table 1. It is seen that selectivity was greatly reduced when zirconium oxide was used as carrier.

COMPARATIVE EXAMPLE 10

A catalyst of the following composition was prepared according to the procedure of Example 36:

$Pd^5$—$Bi^2$—$Pb^1$/$TiO_2$

Using this catalyst, methyl methacrylate was synthesized according to the same procedure as in Example 1. The analytical result of the product is shown in Table 1. It is seen that selectivity was greatly reduced when titanium dioixde was used as carrier.

COMPARATIVE EXAMPLE 11

A catalyst of the following composition was prepared according to the procedure of Example 36:

$Pd^5$—$Bi^2$—$Pb^1$/$MgCO_3$

Using this catalyst, methyl methacrylate was synthesized according to the same procedure as in Example 1. The analytical result of the product is shown in Table 1. It is seen that both conversion and selectivity were greatly reduced when magnesium carbonate was used as carrier.

TABLE 1

|   | Catalyst composition | Conversion (%) | Selectivity (%) |
|---|---|---|---|
| Example |  |  |  |
| 1 | $Pd^5$—$Bi^2$—$Fe^1$/$CaCO_3$ | 75.8 | 97.3 |
| 2 | $Pd^5$—$Bi^2$—$Zn^1$/$CaCO_3$ | 73.1 | 95.4 |
| 3 | $Pd^5$—$Bi^2$—$Ba^1$/$CaCO_3$ | 73.3 | 96.0 |
| 4 | $Pd^5$—$Bi^2$—$Ge^1$/$CaCO_3$ | 74.1 | 95.8 |
| 5 | $Pd^5$—$Bi^2$—$Fe^1$/$CaCO_3$ | 84.6 | 96.8 |
| 6 | " | 73.0 | 96.8 |
| 7 | " | 46.5 | 99.4 |
| 8 | " | 60.8 | 98.3 |
| 9 | $Pd^5$—$Bi^3$—$Fe^1$/$CaCO_3$ | 83.8 | 98.3 |
| 10 | $Pd^{10}$—$Bi^4$—$Fe^1$/$CaCO_3$ | 89.6 | 97.0 |
| 11 | $Pd^5$—$Bi^2$—$Ba^1$/$CaCO_3$ | 81.8 | 98.1 |
| 12 | $Pd^5$—$Bi^2$—$Pb^1$—$Fe^1$/$CaCO_3$ | 83.9 | 98.1 |
| 13 | $Pd^5$—$Bi^2$—$Pb^1$—$Zn^1$/$CaCO_3$ | 80.5 | 95.6 |
| 14 | $Pd^5$—$Bi^2$—$Pb^2$—$Zn^1$/$CaCO_3$ | 80.0 | 95.8 |
| 15 | $Pd^5$—$Bi^2$—$Pb^1$—$Ba^1$/$CaCO_3$ | 81.0 | 97.3 |
| 16 | $Pd^5$—$Bi^2$—$Pb^1$—$Ge^1$/$CaCO_3$ | 82.8 | 97.1 |
| 17 | $Pd^5$—$Bi^2$—$Pb^1$—$Fe^1$/$CaCO_3$ | 92.1 | 96.7 |
| 18 | " | 79.8 | 96.8 |
| 19 | " | 53.7 | 99.4 |
| 20 | " | 70.3 | 99.3 |
| 21 | $Pd^5$—$Bi^3$—$Pb^1$—$Fe^1$/$CaCO_3$ | 87.4 | 98.9 |
| 22 | $Pd^{10}$—$Bi^3$—$Pb^1$—$Fe^1$/$CaCO_3$ | 93.6 | 97.7 |
| 23 | $Pd^5$—$Bi^2$—$Pb^1$—$Ge^1$/$CaCO_3$ | 90.2 | 98.6 |
| 24 | $Pd^5$—$Pb^1$—$Fe^1$/$CaCO_3$ | 89.2 | 96.0 |
| 25 | $Pd^5$—$Pb^1$—$Cr^1$/$CaCO_3$ | 80.7 | 94.8 |
| 26 | $Pd^5$—$Pb^1$—$Co^1$/$CaCO_3$ | 81.2 | 94.7 |
| 27 | $Pd^5$—$Pb^1$—$Zn^1$/$CaCO_3$ | 80.6 | 95.3 |
| 28 | $Pd^5$—$Pb^1$—$Ag^1$/$CaCO_3$ | 81.8 | 94.9 |
| 29 | $Pd^5$—$Pb^1$—$Fe^1$—$Zn^{0.5}$/$CaCO_3$ | 83.5 | 95.1 |
| 30 | $Pd^5$—$Pb^1$—$Fe^1$/$CaCO_3$ | 85.4 | 95.8 |
| 31 | " | 79.8 | 94.5 |
| 32 | " | 50.7 | 98.9 |
| 33 | " | 64.3 | 98.2 |
| 34 | $Pd^5$—$Pb^2$—$Fe^1$/$CaCO_3$ | 85.1 | 95.5 |
| 35 | $Pd^5$—$Pb^1$—$Fe^1$/$CaCO_3$ | 85.0 | 95.7 |
| 36 | $Pd^5$—$Bi^2$—$Pb^1$/$ZnO$ | 76.9 | 96.8 |
| 37 | $Pd^5$—$Bi^2$—$Pb^2$/$ZnO$ | 80.5 | 96.1 |
| 38 | $Pd^5$—$Bi^2$—$Fe^1$/$ZnO$ | 78.8 | 97.6 |
| 39 | $Pd^5$—$Bi^2$—$Mn^1$/$ZnO$ | 82.6 | 95.5 |
| 40 | $Pd^5$—$Bi^2$—$Co^1$/$ZnO$ | 81.4 | 96.9 |
| 41 | $Pd^5$—$Bi^2$—$Ni^1$/$ZnO$ | 81.7 | 96.8 |
| 42 | $Pd^5$—$Bi^2$—$Cu^1$/$ZnO$ | 79.5 | 95.3 |
| 43 | $Pd^5$—$Bi^2$—$Zn^1$/$ZnO$ | 79.3 | 95.4 |
| 44 | $Pd^5$—$Bi^2$—$Ge^1$/$ZnO$ | 81.7 | 95.3 |
| 45 | $Pd^5$—$Bi^2$—$Ba^1$/$ZnO$ | 78.0 | 96.6 |
| 46 | $Pd^5$—$Bi^2$—$Te^1$/$ZnO$ | 79.2 | 94.8 |
| 47 | $Pd^5$—$Bi^2$—$Pb^1$/$ZnO$ | 88.2 | 95.8 |
| 48 | " | 76.3 | 96.0 |
| 49 | " | 48.9 | 98.5 |
| 50 | " | 68.2 | 97.7 |

TABLE 1-continued

|   | Catalyst composition | Conversion (%) | Selectivity (%) |
|---|---|---|---|
| 51 | $Pd^5$—$Bi^3$—$Pb^1$/$ZnO$ | 83.4 | 98.1 |
| 52 | $Pd^5$—$Bi^2$—$Pb^1$—$Fe^1$/$ZnO$ | 87.5 | 97.8 |
| 53 | $Pd^5$—$Bi^2$—$Pb^1$/$ZnO$ | 85.5 | 97.9 |
| Comp. Example |  |  |  |
| 1 | $Pd^5$—$Bi^2$/$CaCO_3$ | 69.5 | 89.3 |
| 2 | $Pd^5$—$Bi^2$—$Fe^1$/$MgO$ | 88.6 | 47.2 |
| 3 | $Pd^5$—$Bi^2$—$Pb^1$/$CaCO_3$ | 72.5 | 92.0 |
| 4 | $Pd^5$—$Bi^2$—$Pb^1$—$Fe^1$/$MgO$ | 90.2 | 46.8 |
| 5 | $Pd^5$—$Pb^1$/$CaCO_3$ | 75.5 | 88.3 |
| 6 | $Pd^5$—$Pb^1$—$Fe^1$/$MgO$ | 82.6 | 43.4 |
| 7 | $Pd^5$—$Bi^2$/$ZnO$ | 73.8 | 88.6 |
| 8 | $Pd^5$—$Bi^2$—$Pb^1$/$MgO$ | 89.5 | 47.0 |
| 9 | $Pd^5$—$Bi^2$—$Pb^1$/$ZrO_2$ | 72.5 | 8.4 |
| 10 | $Pd^5$—$Bi^2$—$Pb^1$/$TiO_2$ | 71.5 | 8.0 |
| 11 | $Pd^5$—$Bi^2$—$Pb^1$/$MgCO_3$ | 23.0 | 41.5 |

What is claimed is:

1. A catalyst for the production of carboxylic acid esters for use in reacting an aldehyde with an alcohol in a liquid phase in the presence of molecular oxygen, comprising calcium carbonate and palladium, bismuth and at least one element selected from the group consisting of barium, iron, zinc and germanium, these elements being supported on said calcium carbonate.

2. A catalyst for the production of carboxylic acid esters for use in reacting an aldehyde with an alcohol in a liquid phase in the presence of molecular oxygen, comprising calcium carbonate and palladium, bismuth, lead and at least one element selected from the group consisting of barium, iron, zinc and germanium, these elements being supported on said calcium carbonate.

3. A catalyst for the production of carboxylic acid esters for use in reacting an aldehyde with an alcohol in a liquid phase in the presence of molecular oxygen, comprising calcium carbonate and palladium, lead and at least one element selected from the group consisting of chromium, iron, cobalt, zinc and silver, these elements being supported on said calcium carbonate.

4. A catalyst for the production of carboxylic acid esters for use in reacting an aldehyde with an alcohol in a liquid phase in the presence of molecular oxygen, comprising zinc oxide and palladium, bismuth and at least one element selected from the group consisting of lead, iron, manganese, cobalt, nickel, copper, zinc, germanium, barium and tellurium, these elements being supported on said zinc oxide.

5. A process for producing a carboxylic acid ester, which comprises reacting an aldehyde with an alcohol in a liquid phase in the presence of molecular oxygen by using at least one catalyst selected from those of any one of claims 1–4.

6. A process for producing a carboxylic acid ester, which comprises reacting an aldehyde with an alcohol in a liquid phase in the presence of molecular oxygen by using a regenerated catalyst obtained by subjecting a catalyst, which has been used in the process of claim 5 and decreased in activity, to a treatment at 0°–100° C. for 0.1–50 hours in the presence of a reducing agent.

* * * * *